United States Patent

Obel et al.

[11] Patent Number: 5,871,507
[45] Date of Patent: Feb. 16, 1999

[54] IMPLANTABLE CARDIAC ASSIST DEVICE HAVING DIFFERENTIAL SIGNAL DETECTION BETWEEN UNIPOLAR ATRIAL AND VENTRICULAR LEADS USING SIGNAL MORPHOLOGY ANALYSIS

[75] Inventors: Martin Obel, Danderyd; Hans Stranberg, Sundbyberg, both of Sweden; Wyn Davies, London, England

[73] Assignee: Pacesetter AB, Järfälla, Sweden

[21] Appl. No.: 870,935

[22] Filed: Jun. 6, 1997

[51] Int. Cl.$^6$ ................................................ A61N 1/365
[52] U.S. Cl. ................................................ 607/9
[58] Field of Search ................................ 607/9, 11, 20, 607/27, 28

[56] References Cited

U.S. PATENT DOCUMENTS

| | | |
|---|---|---|
| 4,905,708 | 3/1990 | Davies . |
| 5,417,718 | 5/1995 | Kleks et al. . |
| 5,458,623 | 10/1995 | Lu et al. . |
| 5,571,143 | 11/1996 | Hoegnelid et al. .......................... 607/9 |
| 5,607,457 | 3/1997 | Schuller ...................................... 607/9 |

FOREIGN PATENT DOCUMENTS 0 465 241  1/1992  European Pat. Off. .
0 646 390  4/1995  European Pat. Off. .

OTHER PUBLICATIONS

"Detection of Pathological Tachycardia by Analysis of Electrogram Morphology," Davies, et al., PACE, vol. 9, Mar.–Apr., 1986, pp. 200–208.

*Primary Examiner*—Scott M. Getzow
*Attorney, Agent, or Firm*—Hill & Simpson

[57] ABSTRACT

A heart stimulator, operable for single-chamber and/or dual-chamber pacing, includes a first unipolar electrical lead placeable in the atrium of a heart, and a second unipolar electrical lead placeable in the ventricle of the heart. In the heart stimulator, a differential detector is connected to each of these unipolar leads and detects a differential signal representative of cardiac activity between the atrial electrode and the ventricular electrode. The differential signal is supplied to decision logic which evaluates each of those outputs including using a morphology analysis, if necessary. Depending on the type of cardiac activity identified as a result of the evaluation, the decision logic supplies a signal to a control unit in the heart stimulator to cause the therapy administered by the heart stimulator to be altered as warranted. The decision logic may also derive a respiration signal from the differential signal, which can also be used to modify the administered therapy.

8 Claims, 4 Drawing Sheets

A IEGM SEMI-BI

1/4 SEC

A IEGM SEMI-BI

SURFACE ECG 1.0 SEC

IMPLANTABLE CARDIAC ASSIST DEVICE HAVING DIFFERENTIAL SIGNAL DETECTION BETWEEN UNIPOLAR ATRIAL AND VENTRICULAR LEADS USING SIGNAL MORPHOLOGY ANALYSIS

BACKGROUND OF THE INVENTION

1. Field of the Invention

The present invention is directed to a cardiac assist device, such as pacemaker, defibrillator or cardioverter, of the type having a unipolar atrial lead and a unipolar ventricular lead, and more particularly to an arrangement in such a device for analyzing the differential signal between the unipolar leads to identify various types of cardiac events and cardiac activity which produced the differential signal.

2. Description of the Prior Art

In the field of implanted cardiac assist devices, such as pacemakers, defibrillators and cardioverters, it is known to employ leads implanted in or around the heart in order to obtain electrical signals which are representative of cardiac events and/or cardiac activity in the heart. Various types of sensing arrangements are known for this purpose. For example, unipolar atrial sensing takes place using the tip electrode on the electrode lead which is also used for delivering pacing pulses to the atrium, with sensing taking place between the tip electrode, functioning as an active sensing electrode, and the metallic pacemaker housing, functioning as the indifferent electrode. Similarly, unipolar ventricular sensing can be accomplished using the tip electrode of an electrode cable placed in the ventricle, operated as a sensing electrode, and the metallic pacemaker housing as the indifferent electrode. Such unipolar sensing has the advantage of requiring only one electrical conductor to be contained within the particular electrode cable which is employed, thereby minimizing the diameter of the cable, and allowing a simplified cable structure, since the same electrode (the tip electrode) is used for pacing and sensing.

Another common form of cardiac activity sensing employed in implanted cardiac assist devices is bipolar sensing. For bipolar sensing, the particular lead which is used (i.e., the atrial lead, the ventricular lead, or both leads) has, in addition to the tip electrode, a ring electrode spaced a distance from the tip electrode, with sensing taking place between the tip electrode and this ring electrode. Because the signal path in bipolar sensing between the two electrodes is much shorter than in the case of unipolar sensing, the sensed signal is less cluttered with noise in comparison to a unipolar signal, since the relatively large amount of intervening tissue between the unipolar electrode and the pacemaker housing allows an opportunity for various types of noise signals to become superimposed on the actual signal produced by the cardiac event or cardiac activity. Such conventional bipolar sensing, however, has the disadvantage that it requires two electrical conductors, and associated insulation to insulate the two conductors from each other, to be contained within the implanted lead, thereby increasing the lead diameter.

A relatively recent sensing approach, differing from conventional unipolar sensing and conventional bipolar sensing, is differential sensing, sometimes also referred to as "combipolar" sensing. In this type of sensing, a unipolar lead is placed in the ventricle and a unipolar is placed in the atrium, and sensing takes place between the respective tip electrodes of these two unipolar leads. A differential signal is produced between these two leads. Sensing of this type is described in U.S. Pat. No. 5,571,143. Atrial activity is sensed between the atrial tip electrode and the ventricular electrode, while ventricular electrical activity is sensed between the tip electrode in the ventricle and the metallic housing of the pacemaker. Such a differential sensing arrangement avoids interference, such as from muscular activity, which particularly arises in the case of conventional unipolar atrial sensing, since the atrial signal is by far the weaker signal compared to the ventricular signal, but there is no need to employ a bipolar electrode in the atrium.

Since the resulting signals in differential sensing can represent activity arising in the atrium as well as activity arising in the ventricle, in order to analyze such a differential signal, there must be provided a way to identify which chamber produced the electrical activity represented in an incoming differential signal. One such approach is described in U.S. Pat. No. 5,607,457 wherein the incoming electrical signals are differentially sensed between the unipolar atrial electrode and unipolar ventricular electrode, and the sensed signal is additionally subjected to a correlation detection in order to identify which electrode is the source for the incoming signal.

In the case of conventional (i.e., non-differential) unipolar sensing, as well as in the case of conventional bipolar sensing, a large number of analysis techniques and algorithms are known for analyzing the sensed signals and identifying the type of cardiac event or cardiac activity which produced the signal for the purpose of classifying the incoming signal. Such classification, in turn, can be used for a number of different purposes, such as determining whether the signal represents normal (or desired) cardiac activity which is not in need of a change in the cardiac assist regimen, such as the pacing regimen, as well as for identifying whether some type of adjustment in the electrical therapy being administered by the cardiac assist device is needed, such as by increasing the pulse amplitude, for example, if an evoked response following an emitted pacing pulse is not detected in the sensed signal. Such classification can also be used to identify critical cardiac events which are in need of immediate attention by the cardiac assist device, such as the presence of tachycardia and/or fibrillation.

One such known technique employed in conventional unipolar sensing and conventional bipolar sensing is a pattern recognition, or waveform morphology, technique. A number of different versions of this technique are known in the art, but in general the technique involves identifying a pattern or waveform shape in all or a portion of the incoming signal representing a cardiac cycle and comparing this pattern or morphology to a number of stored patterns, each indicative of a different type of cardiac event or cardiac activity. The incoming signal is then classified according to the event or activity which is represented by the stored signal most closely resembling the pattern or morphology in the incoming signal. The pattern, in stored form, can be characterized in any of a number of different ways, such as by the occurrence of and/or the amplitude of peaks, the slope of various portions of the signal, as represented by a first differentiation of the signal, or changes in this slope, as represented by a second differentiation of the signal. Various combinations of these characteristics can also be employed to define the pattern even more precisely. Examples of these types of techniques employed in conventional unipolar and/or bipolar sensing are described in U.S. Pat. No. 4,905,708 and in the article entitled "Detection of Pathological Tachycardia by Analysis of Electrogram Morphology," Davies et al., PACE, Vol. 9, March–April 1986, pp. 200–208.

SUMMARY OF THE INVENTION

It is an object of the present invention to provide an arrangement in a cardiac assist device having a unipolar atrial lead and a unipolar ventricular lead which employs differential sensing in order to identify and classify cardiac activity, wherein the identification and classification of the cardiac activity is improved.

The above object is achieved in accordance with the principles of the present invention based on the recognition that morphology analysis of the type used in conventional (non-differential) unipolar sensing and conventional bipolar sensing can be used for analyzing a differential signal. Accordingly, the above object is achieved in a cardiac assist device, such as a pacemaker, having a unipolar atrial lead and a unipolar ventricular lead, wherein differential sensing takes place between the atrial and ventricular lead and between the ventricular lead and the metallic pacemaker housing, and wherein the sensed differential signal is evaluated, if necessary, employing a morphology analysis. In the cardiac assist device disclosed herein, the signal obtained between the atrial tip electrode and the ventricular tip electrode can, if necessary, be evaluated by a morphology analysis method or algorithm, which allows a distinguishing between P-waves, PAC (premature atrial contractions), atrial fibrillation, R-waves, PVC (premature ventricular contractions), and ventricular tachycardia. The inventors have recognized that a significant difference in morphology exists among the differential signals which are produced when these various types of cardiac activity are respectively present, and that recognition of these different types of differential signals, and thus classification of the cardiac activity represented in those signals, can be reliably and relatively simply accomplished.

The morphology analysis, if undertaken, is accomplished in a microprocessor in the decision logic of the implanted device. Since morphology analysis, such as by pattern recognition, requires somewhat complicated processing, this can be a factor in contributing to increased power consumption. Since a desire to maintain power consumption to as low a level as is possible is a goal in most implanted devices, the invention provides that the microprocessor will undertake the morphology analysis only if simpler techniques, which consume less power than the morphology analysis, fail to provide a definitive classification of the differential signal. For example, if no extraordinary conditions, such as fibrillation, as present in the heart, and a relatively normal differential signal is therefore present, this normal signal will exhibit components which can be used to relatively easily identify the source of origin of the signal (i.e., atrium or ventricle) without resorting to morphology analysis. This can be accomplished, for example, by analyzing the energy content of the signal or by analyzing the slew rate of various portions of the signal. Only if this type of preliminary analysis fails to provide an unambiguous result would the microprocessor then resort to the use of morphology analysis.

The morphology analysis which is undertaken may be of the type described in the aforementioned Davies et al. article.

Another approach is to employ a neural network to analyze the differential signal, the neural network having appropriately weighted neurons in order to make appropriate choices for classifying the signal among a number of learned conditions. In the case of morphology analysis, the classification takes place according to stored patterns which must be programmed into the pacemaker memory. These patterns are, at least initially, patterns which have been obtained from an appropriate patient population and which are known to be representative of particular types of cardiac activity. After the cardiac assisted device has been implanted in a subject for awhile, however, a sufficiently large data base of that subject's own cardiac activity will have been established, so that it is possible to replace, or update, the initially entered patterns with patterns which are more precisely representative of the subject in whom the cardiac assist device is implanted. In a neural network, the network learns the subject's cardiac activity history over time by appropriately adjusting the neuron weights. Moreover, the neural network itself can employ fuzzy logic, or can be connected to fuzzy logic processing electronics, in order to make decisions according to the principles of fuzzy logic.

Upon identification and classification of the particular type of cardiac activity which is represented in an incoming differential signal, the therapy being administered by the cardiac assist device can be appropriately adjusted, if necessary, or immediate emergency steps can be undertaken, such as by initiating defibrillation or initiating an anti-tachyarrhythmia routine, when warranted.

DESCRIPTION OF THE PREFERRED EMBODIMENTS

Figure 1:
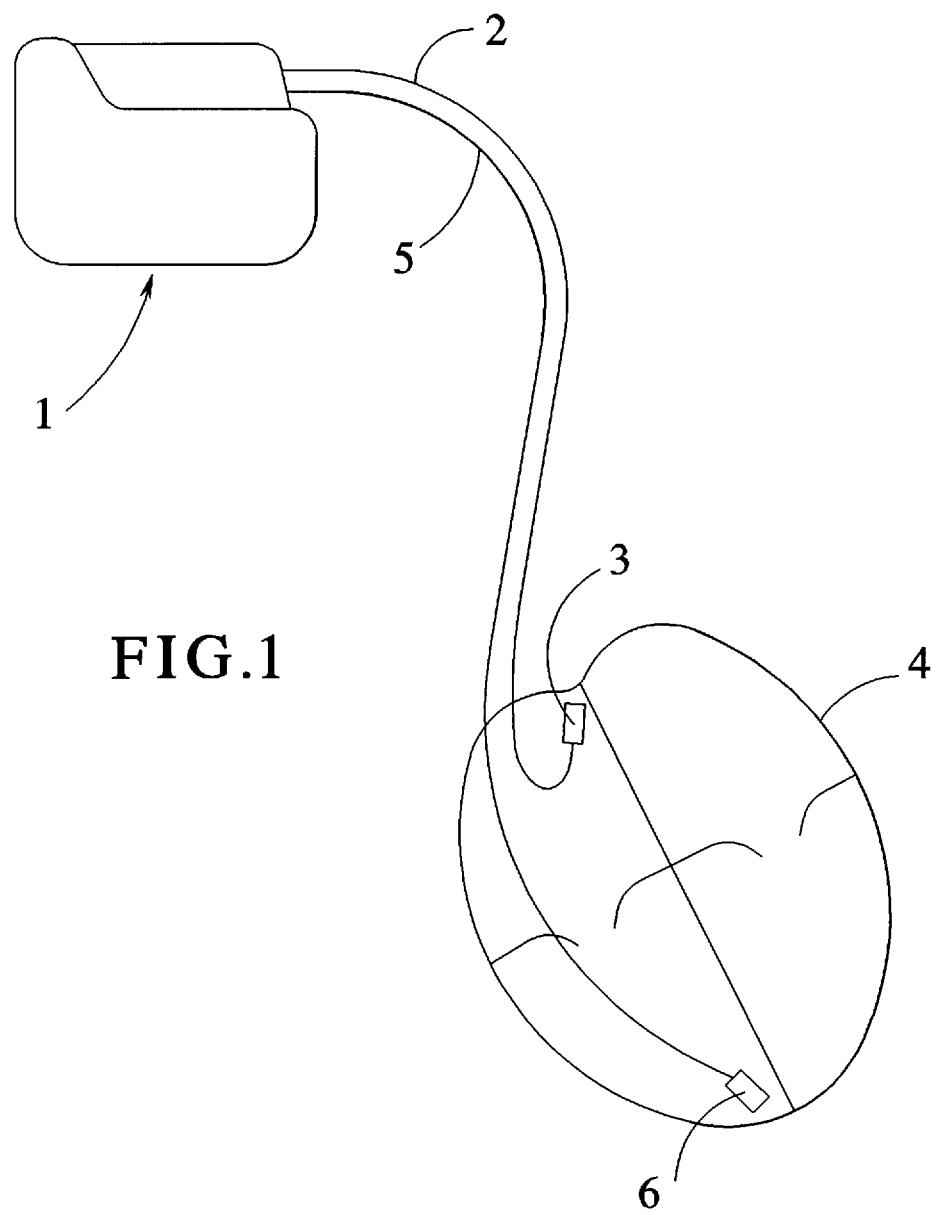
FIG. 1 illustrates the connection of a pacemaker connected to a heart in a known configuration for differential sensing.

FIG. 1 illustrates an implantable pacemaker 1 for stimulating and sensing cardiac activity in vivo in a (schematically illustrated) heart 4. The pacemaker 1 is in electrical connection with the heart 4 by means of a unipolar atrial lead 2 and a unipolar ventricular lead 5. The atrial lead 2 terminates in an electrode 3 disposed at a suitable location in the right atrium of the heart 4, and the ventricular lead 5 terminates in an elect rode 6 disposed at a suitable location in the right ventricle of the heart 4. The respective positions of the electrodes 3 and 6 within the heart 4 shown in FIG. 1 are for exemplary purposes only; the electrodes 3 and 6 can be placed at any suitable locations respectively in the right atrium and the right ventricle in accordance with the physiology and pacing therapy associated with a particular patient. Moreover, only one lead and electrode may be used (active) i.e., only the atrial electrodes 3 or only the ventricular electrode 6, in the case of single-chamber pacing, although both leads and electrodes will still be present.

Figure 2:
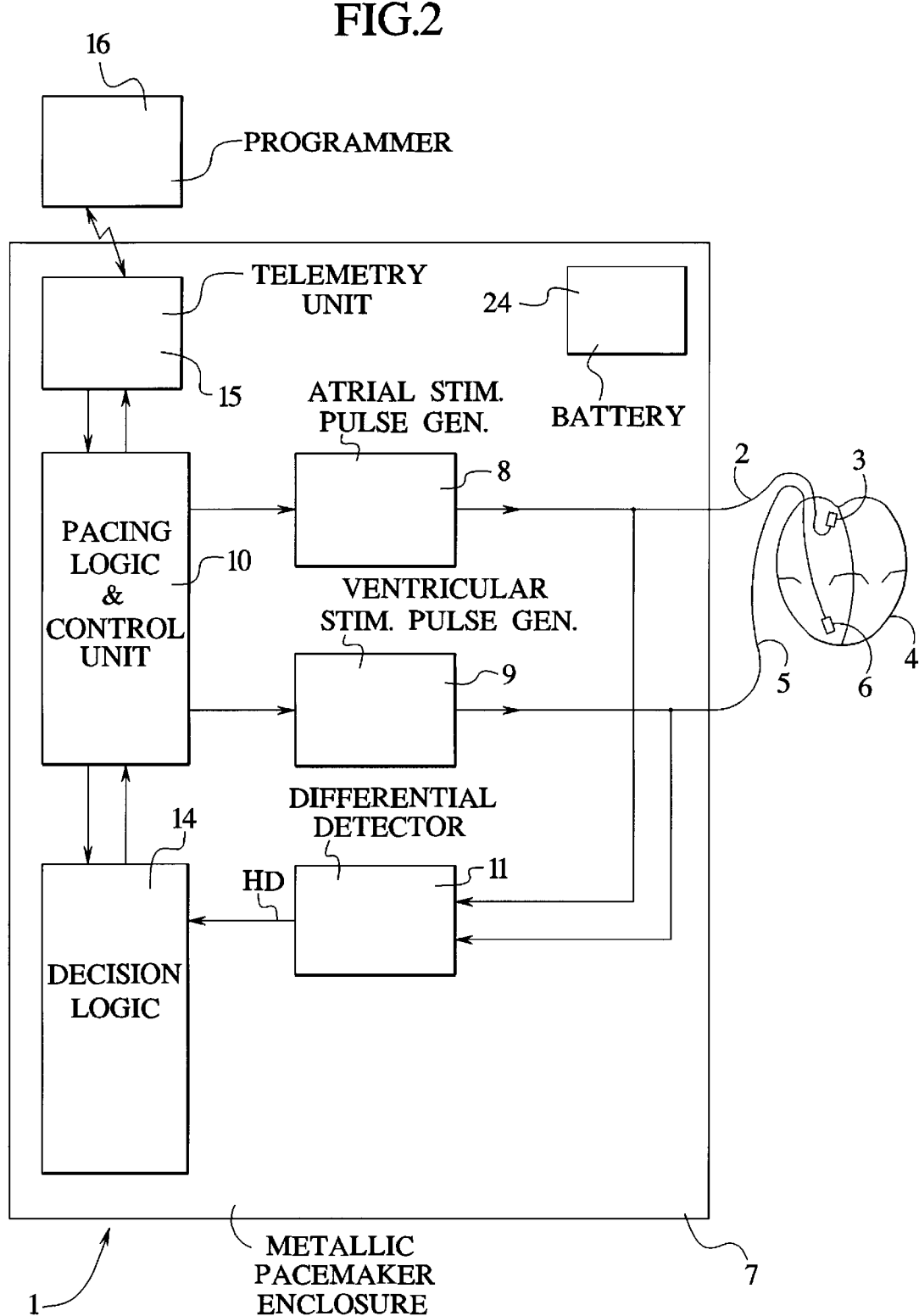
FIG. 2 is a block circuit diagram of the basic components of a cardiac assist device, in the form of a pacemaker, constructed in accordance with the principles of the present invention.

The basic components of the implantable pacemaker 1 are shown in FIG. 2, in accordance with the principles of the present invention. The pacemaker 1 has a metallic pacemaker enclosure 7 to which the leads 2 and 5 are mechanically and electrically connected in a known manner (not shown in greater detail). Electrical pulses for artificially stimulating the atrium of the heart 4 are generated by an atrial stimulation pulse generator 8, connected to the atrial lead 2, and are delivered to the right atrium via the lead 2 and the electrode 3. In a similar manner, ventricular stimulation pulses are generated by a ventricular stimulation pulse generator 9, and are supplied to the right ventricle of the heart 4 via the ventricular lead 5 and the electrode 6. The duration, energy content, rate and other standard features of the atrial and ventricular stimulation pulses are set by means of a pacing logic and control unit 10, connected to the atrial stimulation pulse generator 8 and to the ventricular stimulation pulse generator 9. The pacing logic and control unit 10 contains all of the necessary, known electronics, which may include a microprocessor and a memory, for operating a programmable implanted pacemaker.

Detection of atrial and ventricular cardiac events also takes place via the unipolar leads 2 and 5. For this purpose, the atrial lead 2 is connected to a differential detector 11. The ventricular lead 5 is also connected to the differential detector 11. Detecting therefore always takes place in the differential detector 11 between the atrial electrode 3 and the ventricular electrode 6.

The output of the differential detector 11 is supplied to decision logic 14. The decision logic 14 employs a morphology analysis of any suitable type, such as that disclosed in the aforementioned Davies et al. article, in order to evaluate and classify each of the signals produced by the differential detector 11. Based on this morphology evaluation, the decision logic 14 supplies a signal to the pacing logic and control unit 10 indicating whether any remedial steps should be undertaken to adjust the pacing regimen.

Although not shown in FIG. 2, the pacing-related components shown in FIG. 2 can be employed in a defibrillator or cardioverter, which also has the capability of storing sufficient energy to effect cardioversion or defibrillation of a heart in need of such therapy. If the components shown in FIG. 2 are employed in such an implanted device, the output of the decision logic 14 can also be used to initiate, when warranted, cardioversion or defibrillation.

In addition to providing assistance for artificially maintaining a normal sinus rhythm by ventricular and/or atrial pacing, it is well known to store an anti-tachyarrhythmia routine in the pacing logic and control unit 10, and such a routine can be initiated upon an identification in the decision logic 14 that such activity is present.

All components in FIG. 2 are supplied with power by a battery 24 contained in the pacemaker enclosure 7. Electrical connections from the battery 24 to each of the components are not separately shown, these being well-known to those of ordinary skill in the art. The pacing logic and control unit 10 contains standard circuitry for setting the energy content of the atrial and ventricular pulses respectively generated by the pulse generators 8 and 9 so as to be just enough to evoke an appropriate response upon delivery of those pulses to the heart 4, thereby conserving the power of the battery 24. The pacing logic and control unit 10 also includes suitable demand circuitry so that pulses are caused to be emitted by the pulse generators 8 and 9 only in the absence of natural or spontaneous atrial and/or ventricular activity. The pacing logic and control unit 10 can, per programmed instructions, operate the pulse generators 8 and/or 9 for single-chamber or dual-chamber pacing.

The pacing logic and control unit 10 is also in two-way communication with a telemetry unit 15, the telemetry unit 15, in turn, being in duplex communication with an extracorporeal programmer 16, such as by RF communication. The programmer 16 is used not only to program the operation of the pacemaker 1, but also to enter new or updated operating parameters into the pacing logic and control unit 10 for use in the operating program. The programmer 16 is also used to periodically download accumulated, stored historical information regarding the operation of the pacemaker 1, and the state of the heart 4, over an extended period of time.

Figure 3:
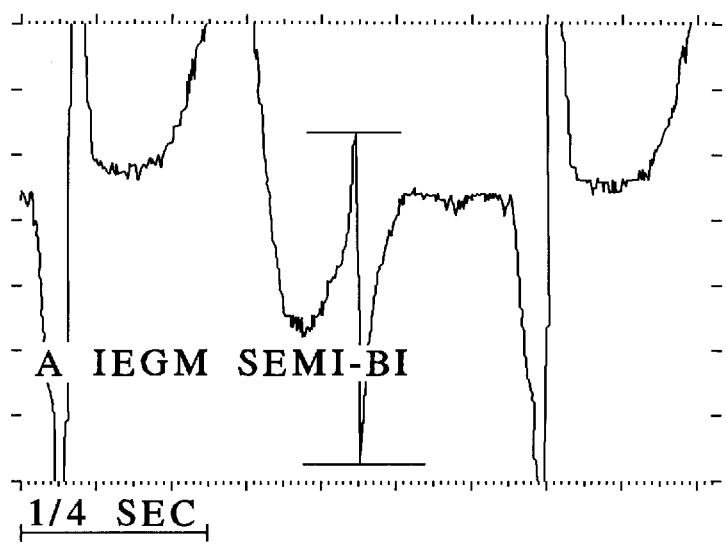
FIG. 3 shows a first waveform, representing normal atrial activity, obtained by differential sensing, which is to be subjected to a morphology analysis in the cardiac assist device of FIG. 2.
Figure 4:
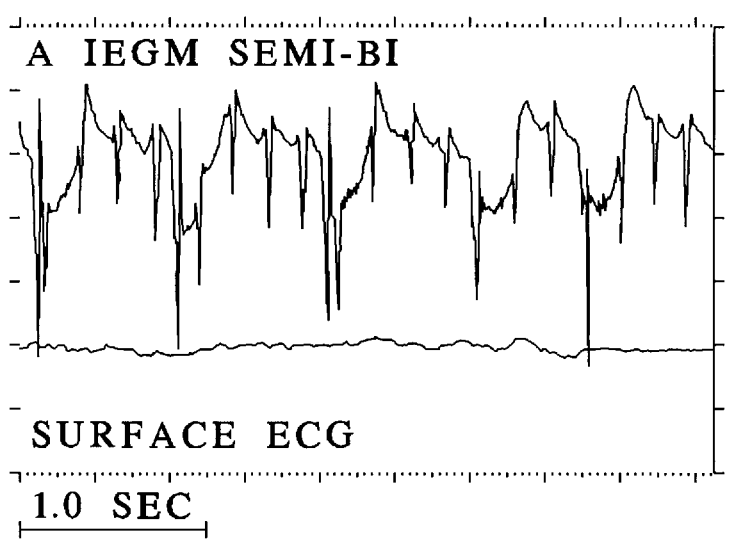
FIG. 4 shows a differential waveform arising in the atrium, representative of atrial fibrillation, to be subjected to morphology analysis in the cardiac assist device of FIG. 2.

Exemplary waveforms of the type appearing at the output of the differential detector 11 are shown in FIGS. 3 and 4. FIG. 3 represents a differential signal indicative of normal cardiac activity. This signal would appear at the output of the differential detector 11 when the heart 4 is functioning normally.

These signals, when the heart 4 is experiencing these respective types of activities, are subjected to the aforementioned analysis in the decision logic 14. In the case of the signal shown in FIG. 3, the output of the decision logic 14 would inform the pacing logic and control unit 10 to maintain its current status, i.e., no changes in the administration of the pacing regimen are needed. In the case of of the signal shown in FIG. 4 being supplied to the decision logic 14, the decision logic 14 would identify, by morphology analysis, the fact that atrial fibrillation is occurring, and would provide a signal to the pacing logic and control unit 10 identifying the presence of this type of activity. According to stored routines therein, the pacing logic and control unit 10 can then adjust the pulses, in terms of amplitude and/or frequency, supplied to the atrium in order to attempt to correct this abnormality. If and when the heart 4 exits atrial fibrillation (this usually not being a life-threatening occurrence) the decision logic 14 will again recognize the presence of a waveform of the type shown in FIG. 3, and will inform the pacing logic and control unit 10 that it should revert to a "normal" pacing regimen.

Figure 6:
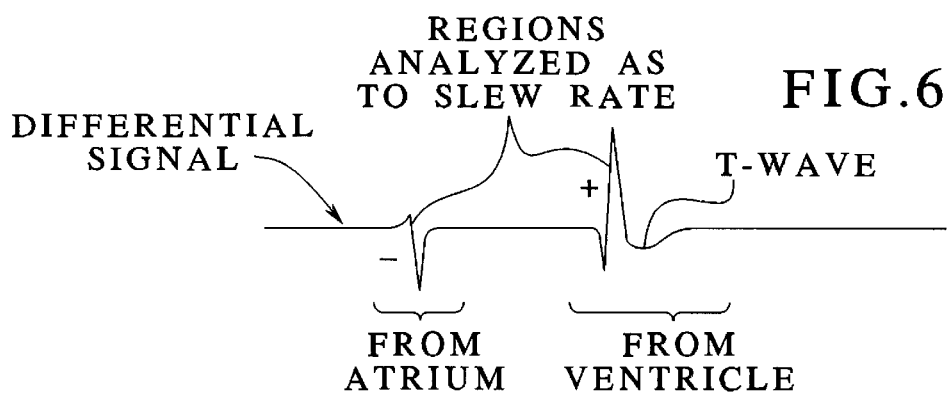
FIG. 6 is a simplified illustration of a differential signal for explaining different classification techniques in accordance with the invention.

Although it is possible for the decision logic 14 to rely exclusively on a morphology analysis for classifying the differential signal received from the differential detector 11, undertaking such a morphology analysis, such as by pattern recognition, involves an increased amount of processing time, when the morphology analysis is done in a microprocessor. This results in an elevated power drain on the battery 24. In the context of most implanted cardiac assist devices, it is desirable to maintain the power drain on the battery as low as possible. Therefore, as shown in FIG. 6, the cardiac assist device constructed and operating in accordance with the invention can employ a simplified classification technique, which is less computation-intensive than morphology analysis, in situations wherein the differential signal is relatively straightforward. In most "normal" situations, the differential signal will appear as shown in FIG. 6, and it is therefore not necessarily to resort to morphology analysis in order to classify such a signal, i.e., in order to determine whether the signal originates in the atrium or in the ventricle. Only if more difficult waveforms occur, as will arise, for example, in the case of a fibrillating heart, in which case the simpler techniques would not produce an unambiguous result, would the microprocessor then resort to the use of morphology analysis.

Figure 5:
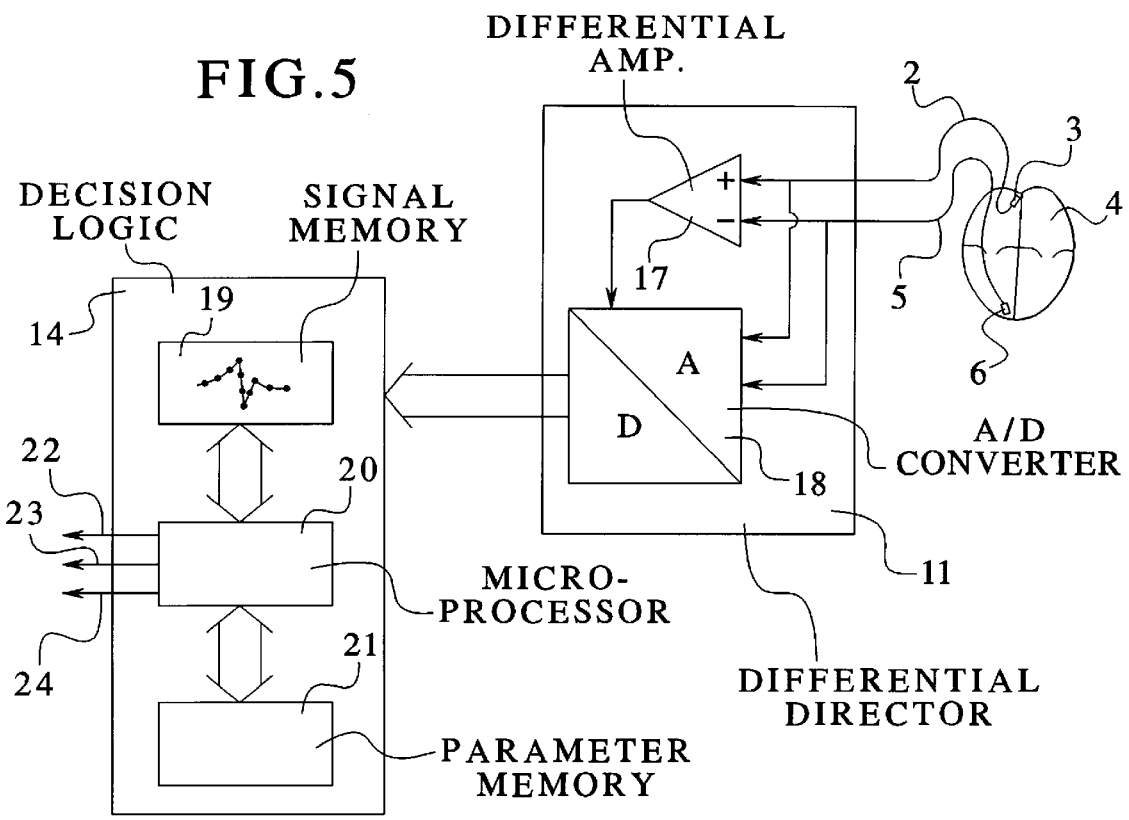
FIG. 5 is a block diagram showing details of the differential detector and the decision logic in the cardiac assist device shown in FIG. 2.

Therefore, in the embodiment shown in FIG. 5, the differential detector 11 includes a differential amplifier 17 connected to the unipolar leads 2 and 5, as well as an analog-to-digital converter 18, to which the unipolar leads 2 and 5 are also connected at the analog input side. The differential amplifier 17 determines the difference between the signals arising on the respective unipolar leads 2 and 5, and supplies an output signal, as a control signal, to the converter 18. When the difference between the signals on the respective unipolar leads 2 and 5 exceeds a predetermined value, the differential amplifier 17 emits an output signal, which initiates sampling of the signals supplied to the analog side of the converter 18. If the difference between the respective signals on the unipolar leads 2 and 5 is below the aforementioned predetermined value, it is assumed that an unambiguous classification of the differential signal using simpler techniques would not be possible, in which case a morphology analysis will then be used to classify the incoming signal.

Assuming that an output is emitted by the differential amplifier 17, a sample representation of the differential signal, in digital form, is then supplied to the decision logic 14. The decision logic 14 includes a signal memory 19 in communication with a microprocessor 20, and a parameter memory 21, also in communication with the microprocessor 20. Successive samples of the differential signal from the converter 18 are stored in the signal memory 19, so that a complete signal, or a representation thereof, becomes stored in the signal memory 19. Assuming that morphology analysis is not needed, the microprocessor 20 can then analyze this storage signal based on a selected parameter thereof. Two possibilities are for the microprocessor 20 to analyze the slew rate of the stored signal or to analyze the energy content of the stored signal.

As can be seen from FIG. 6, the portion of the differential signal which originates in the atrium will have a negative slew rate, and the portion of the signal originating from the ventricle will have a positive slew rate. By analyzing the slew rate merely to determine whether it is positive or negative, an identification can then be made as to whether the differential signal originated in the atrium or in the ventricle. The parameter memory 21 stores the slew rate parameters, i.e., a first slew rate (negative) for atrial signals and a second slew rate (negative) for ventricle signals.

The energy content of the signal can also be used as an indicator to identify the origin of the differential signal. The energy content is expressed as the time integral of the squared signal voltage (amplitude). For this purpose the signal stored in the signal memory 19 is squared, and integration is begun in the microprocessor 20 when the signal exceeds a predetermined level, such as 0.2 mV. Integration is performed until further integration does not add any significant amount (such as a predetermined increment, or a percentage increment) to the running result. It must be ensured, however, that integration is ended before the T-wave occurs, otherwise the result will take too long to analyze. The integration period will typically last approximately 10–25 ms for signals originating in the atrium, and will last approximately 100 ms for signals originating in the ventricle. These integration ranges are stored in the parameter memory 21 as energy content (integration time) parameters respectively for atrial signals and ventricular signals. The microprocessor 20 compares the integration time of the current differential signal to these stored parameters, so as to make a determination as to whether the current signal originated in the atrium or in the ventricle.

Dependent on the outcome of the aforementioned analysis, the microprocessor 20 will emit a signal on line 22 indicating that the current differential signal originated in the atrium, or will emit a signal on line 23 indicating that the current differential signal originated in the ventricle, or, if morphology analysis is used, will emit a signal on line 24 indicating that some type of abnormal cardiac condition, such as fibrillation, is present.

A further application of the invention is to detect the respiration rate of the subject in whom the cardiac assist device operating according to the invention is implanted. The ventricular lead tip 6 is, in most cases, located in the apex in the ventricle. This position is very close to the diaphragm muscle which controls respiration. To reliably detect respiration, an electrode located close to the diaphragm is needed, together with an indifferent electrode which is not too close to the respiration detection electrode, but still is not exposed to significant myopotential noise. One possibility, therefore, is to use the unipolar lead 5 with the tip 6 located in the apex, with the tip 3 of the unipolar lead 2 serving as the indifferent electrode.

Figure 7:
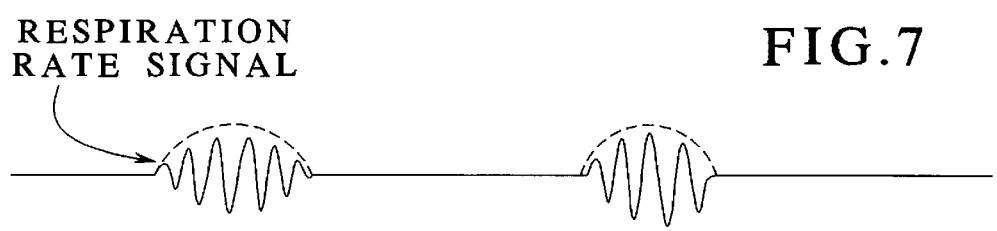
FIG. 7 shows a waveform for a respiration rate signal which can be obtained as a differential signal in the cardiac assist device shown in FIG. 2.

The detection criteria for respiration are a low amplitude signal with a burst characteristic, wherein the frequency in the burst is in the range of 10–25 Hz, and the repetition rate of the burst is similar to the expected human respiration rate. An example of such a signal is shown in FIG. 7. Typically, a signal having the waveform shown in FIG. 7 will have a peak amplitude within the burst which is less than 30 to 50 mV and, as noted above, the waveform within the burst will have a frequency in the range of 10–25 Hz. In order to qualify a signal as a respiration rate signal, one inspiration must include at least five peaks during 200 ms.

In order to detect a respiration signal of the type shown in FIG. 7, the differential detector 11 must be set at a relatively high sensitivity, and thus many non-respiration related artifacts may be present in the signal. Therefore, a respiration rate signal identifying algorithm must take into account factors other than the aforementioned criteria in order to reliably identify the respiration rate. Examples of these other factors are amplitude stability, repetition rate and burst duration. If the differential signal shows a high variability in amplitude and burst duration from burst-to-burst, then the origin of the signal is most likely not respiration. Over time, however, slow variations in such a signal, related to changing physical activity, will still be significant. The respiration rate signal is then used in a known manner to control the pacing rate.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:

a metallic housing implantable in a subject;

pulse generator means contained in said housing for emitting stimulation pulses;

only two sensing electrodes adapted for in vivo interaction with cardiac tissue;

a first unipolar electrical lead being electrically connected to said pulse generator means for receiving said stimulation pulses therefrom and terminating in an atrial electrode placeable in the atrium of a heart of said subject, said atrial electrode comprising a first of said two sensing electrodes;

a second unipolar electrical lead being electrically connected to said pulse generator means for receiving said stimulation pulses therefrom, and terminating in a ventricular electrode placeable in a ventricle of said heart, said ventricular electrode comprising a second of said two sensing electrodes;

control means in said housing for controlling said pulse generator means for setting an amplitude and a rate of said stimulation pulses and for causing said stimulation pulses to be delivered to at least one of the atrium and the ventricle;

differential detector means in said housing connected to said two sensing electrodes via said first and second electrical leads for differentially detecting cardiac activity between said atrial electrode and said ventricular electrode and for generating a differential electrical activity signal corresponding to said cardiac activity; and differential signal analysis means, supplied with said differential signal for analyzing said differential signal for classifying said cardiac activity among a plurality of different types of cardiac activity and for supplying a signal to said control means for causing said control means to alter said stimulation pulses, if necessary.

2. A heart stimulator as claimed in claim 1 further comprising means in said differential signal analysis means for determining an energy content in said differential signal for identifying an origin of said cardiac activity.

3. A heart stimulator as claimed in claim 1 further comprising means in said differential signal analysis means for determining the slew rate in said differential signal for identifying an origin of said cardiac activity.

4. A heart stimulator as claimed in claim 1 further comprising means in said differential signal analysis means for making a gradient pattern detection of said differential signal for identifying an origin of said cardiac activity.

5. A heart stimulator as claimed in claim 1 further comprising means for deriving a respiration rate from said differential signal.

6. A method for pacing a heart comprising the steps of:

implanting only two sensing electrodes in a subject for in vivo interaction with cardiac tissue;

implanting a first unipolar electrical lead in the subject terminating in an atrial electrode in an atrium of the heart of the subject, said atrial electrode comprising a first of said two sensing electrodes;

implanting a second unipolar electrical lead in the subject terminating in an ventricular electrode in an apex of a ventricle of the heart of the subject, said ventricular electrode comprising a second of said two sensing electrodes;

obtaining a differential electrical signal, due to cardiac activity of the subject, between said two sensing electrodes;

deriving a respiration signal from said differential signal; and administering stimulation pulses to said subject via at least one of said first and second unipolar electrical leads, dependent on said respiration signal derived from said differential signal.

7. A method as claimed in claim 6 wherein the step of administering stimulation pulses comprises administering stimulation pulses to said subject via at least one of said first and second unipolar electrical leads at a rate dependent on said respiration signal derived from said differential signal.

8. A method as claimed in claim 6 wherein the step of administering stimulation pulses comprises the steps of:

administering stimulation pulses to said subject at a basic rate; and modifying said basic rate dependent on said respiration signal derived from said differential signal.

* * * * *